United States Patent

Yang et al.

[11] Patent Number: 5,711,977
[45] Date of Patent: Jan. 27, 1998

[54] BIFIDOBACTERIA STRAINS WITH ACID, BILE SALT AND OXYGEN TOLERANCE AND THEIR CULTURE METHOD

[75] Inventors: Yuann-Shiuann Yang; Mei-Ching Chen; Chii-Cherng Liao, all of Hsinchu, Taiwan

[73] Assignee: Food Industry Research and Development Institute, Hsinchu, Taiwan

[21] Appl. No.: 735,263

[22] Filed: Oct. 22, 1996

[30] Foreign Application Priority Data

May 6, 1996 [TW] Taiwan .................. 85106752

[51] Int. Cl.$^6$ .................. A23C 9/12; A01N 63/02; C12N 1/00; C12N 1/38
[52] U.S. Cl. .................. 426/61; 426/34; 426/42; 426/43; 426/565; 426/580; 426/590; 426/660; 424/93.4; 435/243; 435/244; 435/252.1
[58] Field of Search .................. 426/34, 42, 43; 424/93.4; 435/243, 244, 252.1

[56] References Cited

U.S. PATENT DOCUMENTS

| | | | |
|---|---|---|---|
| 4,087,559 | 5/1978 | Mutai | 426/43 |
| 4,091,117 | 5/1978 | Mutai | 426/43 |
| 4,187,321 | 2/1980 | Mutai | 426/43 |
| 4,870,020 | 9/1989 | Sozzi | 435/252.1 |
| 5,087,449 | 2/1992 | Masai | 424/195.1 |
| 5,192,685 | 3/1993 | Yasui | 435/252.1 |
| 5,322,836 | 6/1994 | Tomita | 514/6 |
| 5,494,664 | 2/1996 | Brassart | 424/93.4 |
| 5,501,857 | 3/1996 | Zimmer | 424/438 |

OTHER PUBLICATIONS

Shimamura et al. 1992 J Dairy Sci. 75 pp. 3296–3306, Dec. 1, 1992.
Grill et al. 1995 Current Microbiol. 31 (1) pp. 23–27, Jul. 1, 1995.
Lankaputhra et al. 1995 Cultured Dairy Products Journal 20 (3) pp. 2–7, Aug. 1, 1995.

*Primary Examiner*—Marian C. Knode
*Assistant Examiner*—Many K Zerman
*Attorney, Agent, or Firm*—Bacon & Thomas

[57] ABSTRACT

The present invention relates to bidifobacteria strains having tolerance in the gastrointestinal environments and to a method for culturing the same. The strains of the invention are *Bifidobacterium longum* (ATCC 55815, 55816, 55817, 55818) which have tolerances against bile salt, acid and oxygen and which have been obtained through mutagenesis and screening for tolerances against bile salt, acid and oxygen by using acid-tolerant *Bifidobacterium longum* Y1 and Y2 strains (ATCC 55813 and 55814) isolated from healthy infant feces as the parent strains. The strains of the present invention show excellent growth under aerobic condition in the presence of skim milk without supplement of other growth promoting substances. This oxygen-tolerant property is favor for their industrial production.

12 Claims, No Drawings

BIFIDOBACTERIA STRAINS WITH ACID, BILE SALT AND OXYGEN TOLERANCE AND THEIR CULTURE METHOD

BACKGROUND OF THE INVENTION

1. Field of the Invention

The present invention relates to Bifidobacterium strains having gastric acid-tolerance and strains having additional tolerances against bile salt, gastric acid and oxygen, and to a method for culturing these strains under aerobic conditions. Bifidobacterium is typically used as an indicator or a guarantee for infant having a healthy intestinal bacterial flora. Whereas types and mounts of Bifidobacterium populations varies with different stages of age, however, Bifidobacterium has an important relationship with human health based on the fact that it is present in a whole life cycle of human being and its population tends to decrease as increase of age as well as on the results of its clinical trials.

They have various physiological properties, such as, inhibition of putrefactive and pathogenic bacteria, balance maintaining of normal intstinal bacterial populations, inhibition of production of toxic amines, synthesis of vitamins B groups and procucing of L-lactic acid which is favor for utilized by an infant. However, since bifidobacteria are more anaerobic than other lactic acid bacteria, there are several key points for developing products containing viable bifidobacteria such as, growing ability of bacteria under aerobic condition, difficulties and costs for maintenance of bacterial survivability during storage of products. In addition, after being orally administrated, bacteria will be under stress of gastrointestenal environment and subjected to the specific adsorption of the intestine.

Accordingly, the selection of effective strains will be depended on the tolerant abilities against gastric acid and bile salt of the strain as well as on its isolating source and locality.

2. Description of the Prior Art

The goal of searching a strain having tolerance against oxygen, acid and bile salt is to develop bifidobacteria products. Heretofor, there have been developed near hundred kinds of related products throughout the world, however, none of strains used thereof meets completely the requirements described above. For example, as seen in patents and literatures associated with tolerant strains of Bifidobacterium spp. and producing processes thereof (e.g., Table I and II), there were mainly strains with aicd-tolerance and oxygen-tolerance, wherein those having bile salt-tolerance were less.

Further, according to the results of studies, Bifidobacterium spp. ATCC 15700, ATCC 15696, ATCC 15697 and ATCC 15707 have extremely low growing abilities or can hardly grow when they are cultured in the presence of 0.3% glycocholate for 24 hours. Moreover, studies of the prior art add-tolerant strains have been devoted largely on the bacterial survivability in acidic dairy product (pH 4–4.8) over a period of storage under referigerating conditions, while few studies carried out tests of tolerance against gastric acid increasing, where they set pH value at about 3–3.5 and not at about pH 2 which occurs during serection of gastric juice.

SUMMARY OF THE INVENTION

Accordingly, an object of the present invention is to provide a gastric acid-tolerant strain of *Bifidobacterium longum* ioslated from healthy infant's feces, and, based on said isolated strain, to provide strains of multiple characteristics such as tolerances against gastric acid, bile salt and oxygen by means of artificial mutagenesis and screening.

TABLE I

Comparison of patented bifidobacteria strains with the invention strains

| Strains | Inventors | Isolation sources | Characteristics | Assignee | Reference |
|---|---|---|---|---|---|
| *Bifidobacterium bifidum* YIT-4002(FERM-P 3371) | Mutai et al | Feces of healthy infant fed with mother milk | 1. Aerobic growth without growth promoting substance *Growth up to 5.0 × 10⁹ CFU/ml in the presence of 6.5 ppm oxygen over 24 hours and up to 6.5 × 10⁹ CFU/ml in the presence of 0.1 ppm oxygen over 24 hours | Yakult Honsha | USP4087559(1978) |
| *B. bifidum* YIT-4005-(FERM-P 3372) | Mutai et al | Feces of healthy infant fed with mother milk | 1. Oxygen tolerance, results of growth is same as that of anaerobic growth and can be up to 10⁹ CFU/ml 2. Acid tolerance, 4% survived after stored at pH 4.2 for 7 days(similar results obtained both in milk and in buffer solution) | Yakult Honsha | USP4091117(1978) JP second publication No. Sho-56-42250 (1981) |
| *B. breve* YIT-4006 (FERM-P 3906) | Mutai et al | Feces of healthy infant fed with mother milk | 1. Growth with tolerance against oxygen in absence of growth promoting substances and can be up to 10⁹ CFU/ml after 24 horus | Yakult Honsha | USP4187321(1980) JP second publication No. Sho-59-5303 (1984) |
| *B. breve* HW-107(FERM 5774) | Ishikawa et al | Feces of healthy infant fed with milk | 1. Acid tolerance (gastric acid) pH 3.5, 37° C./1 hour, bacteria population decreased 3.89 log value (buffer system) | Midorina Co., Ltd | JP first publication No. Sho-57-99190 (1982) |
| *B. longum* M-8201(FERM 6548) | Kawashima et al | Feces of healthy infant fed with milk | 1. Acid tolerance 11.8% survived after storing at pH 4.6 for 7 days (buffer system), 53.6% survive after storing at pH 4.8 for 7 days (milk system) | Morinaga Milk Industry Co., Ltd. | JP second publication No. Sho-59-53829 (1984) |
| *B. breve* SBR 3212(FERM 11915) | Yoshimo et al | Feces of healthy infant born several months and fed with mother milk | 1. Acid tolerance 8% survived after storing at pH 4.0 for 7 days (milk system) and 23% (buffer system) 2. Oxygen tolerance growth increased 10-fold after 24 hour culturing and kept at 5-fold increase after 48 hours | Snow Brand Milk Prod Co., Ltd. | JP first publication No. Hei-4-320642 (1992) |
| *B. infantis* CNCM I-372 *B. bifidum* | Sozzi | — | 1. Acid tolerance survivabilities after storing at pH 4.0 for 7 days: 100%(I-372), 75%(I-373) and | Nestec S.A. (Switzerland) | USP4870020 (1989) JP first publication No. Sho-6-205481 |

TABLE I-continued

Comparison of patented bifidobacteria strains with the invention strains

| Strains | Inventors | Isolation sources | Characteristics | Assignee | Reference |
|---|---|---|---|---|---|
| CNCM I-373 B. breve CNCM I-374 | | | 70%(I-374); and after 40 days: 70%(I-372), 60%(I-373) and 14%(I-374) (milk system) 2. Oxygen toleranceing substances with growth promoting substances | | (1986) EP 86101202 (1986) |
| B. longum No. 1022(FERM-P 8033) | Mura et al | UV mutant of B. longum ATCC 15708 | 1. Acid tolerance After storing at pH 4.7 for 7 days, survivability of original B. longum ATCC 15708 is only 7% of that of mutant | Mei Ji Milk Industry Co., Ltd. | JP first publication No. Sho-61-85182 (1986) |
| B. breve M 7204(FERM1324) | Kawashima et al | | 1. Acid tolerance 0.02% survived after storing at pH 4.6 for 7 days (buffer system) 1.5% survived after storing at pH 4.8 for 7 days (milk system) | Morinaga Milk Industry Co., Ltd. | JP second publication No. Sho-47-29995 (1972) |
| B. longum ATCC 55816 | — | Feces of healthy infant | 1. Gastric acid tolerance Population decreased 3–4 log value after treatment at pH 2, 37° C./2 hr (0.85% NaCl/0.01 N HCl system) 2. Tolerance against bile salt Growth up to $10^8$–$10^9$ CFU/ml in the presence of 0.3% oxgall for 24 hours 3. Oxygen tolerance growth up to $10^9$ CFU/ml for 24 hours without growth promoting substances. | — | The present invention |

TABLE II

Comparison of Tolerant Strains Disclosed in the Literature with the Invention Strains

| Strains | Isolation sources | Characteristics | Research Unit | References |
|---|---|---|---|---|
| B. longum TQB 21-2-2 | Feces of mid-age men | 1. Oxygen tolerance Growth increased 25% after thin layer standing for 24 hours Growth increased 25% after shaking for 60 hours | Ten-jin Light Industries College | Been Fa, Sheu-et al. (1994) |
| B. bifidum | — | 1. Oxygen tolerance Growth up to $10^9$ CFU/ml after non-anaerobic culturing for 5–7 hours (milk system) 2. Acid tolerance 13.5% survived after storing at pH 4.5 for 10 days (milk system) | Wuu-Hann Light Industries Research Institute | Sheau Chau, Fuh et al. (1990, 1992) |
| B. bifidum GSNE | Feces of infant fed with milk | 1. Oxygen tolerance Growth increased 1.3 log value in the presence of 6.2–6.4 ppm dissolved oxygen for 24 hours and 1.8 log values in the presence of 0 ppm dissolved oxgen for 24 hours (milk system) | Yakult Honsha Research Institute | Wumada (1982) |
| B. bifidum B. breve | — | 1. Gastric acid tolerance Population decreased 5.3 and 2.6 log values, respectively, after culturing at pH 3, 37° C. for 3 hours (0.2% NaCl, 0.32% pepsin system) 2. Bile salt tolerance Growth rate in the presence of 135 ppm bile salt were 67% and 45%, respectively (culture medium system) | Yakult Honsha Research Institute | Mutai (1978) |
| B. longum | — | 1. Bile salt tolerance Population decreased 2.01 log value at 2% oxgall, 37° C. for 12 hr (distilled water system) | Mississippi State University | Clark and Martin (1994) |
| Bifidobacterium Bb-12 | — | 1. Acid tolerance 100% survived at pH 3 for 2 hours (MRS liquid culturing medium system) 2. Bile salt tolerance 100% survived at 0.5% oxgall, 37° C. for 2 hr (milk plus yeast extract system) | Chr. Hansen's Lab. | Hoier (1992) |
| B. longum ATCC 55816 | Feces of healthy infant | 1. Gastric acid tolerance Population decreased 3–4 log value after treatment at pH 2, 37° C./2 hr (0.85% NaCl/0.01 N HCl system) 2. Tolerance against bile salt Growth up to $10^8$–$10^9$ CFU/ml in the presence of 0.3% oxgall for 24 hours 3. Tolerance against oxygen Growth up to $10^9$ CFU/ml for 24 hours without growth promoting substance | — | The present invention |

DETAILED DESCRIPTION OF THE PREFERRED EMBODIMENT

Deposition of mutant microorganisms (1) The description of microorganism mutants The subject microorganisms of the present invention consist of acid-tolerant strains of *Bifidobacterium longum* Y1 and Y2 (ATCC 55813 and 55814) which have been isolated from feces of healthy infant, and of mutant strains including ATCC 55815, ATCC 55816, ATCC 55817 and ATCC 55818 which have been obtained by using *Bifidobacterium longum* Y 1 and Y2 as parent strains and performing mutagenetic modification. Among them, the former two new strains are mutant strains of parent strain ATCC 55813, while the latter two are mutant strains of parent strains ATCC 55814. The strains of the present invention are characterized by possessing simultaneously tolerances against gastrointestinal environment which contains bile salt and gastric acid, and against oxygen, which is favor for industrial culturing.

Strains of the present invention are deposited at American Type Culture Collection, 12301 Parklawn Drive, Rockville, Md. 20852, under Budapest Treaty, the date and number of deposition are as follow:

| Name of microorganism | Deposition date | Number |
| --- | --- | --- |
| *Bifidobacterium longum* Y1 | August 29, 1996 | ATCC 55813 |
| *B. longum* Y2 | August 29, 1996 | ATCC 55814 |
| *B. longum* Y1-2E-05 | August 29, 1996 | ATCC 55815 |
| *B. longum* Y1-4A-01 | August 29, 1996 | ATCC 55816 |
| *B. longum* Y2-1A-01 | August 29, 1996 | ATCC 55817 |
| *B. longum* Y2-2B-04 | August 29, 1996 | ATCC 55818 |

(2) The culture of new strains

The mutagenesis method, strategy and procedure of screening and isolation as well as compositions of medium for producing of new strains of the present invention will be described in detailed in Examples hereinafter.

(3) Verification of Tolerances (i) Bile salt tolerance

Since oxgall has been commonly used in medium for selectively culturing human intestinal bacteria, its effectiveness should be very similar to human bile salt and its average concentration used is 0.3%(w/v), therefore, after properly activated, 1% each of new strains of the present invention and parent strains were inoculated into culturing solution: (1) basic midium MRS supplemented with 0.3% oxgall as test group, (2) basic medium as control group. After culturing for 24 hours, measure and compare their OD 600 nm and population survived to verify their bile salt tolerance.

(ii) Acid tolerance

The pH value of gastric acid varies in the range of 1.5–4.5 in a period of 2 hours depending on the entering time and type of gastric contents. In the present invention, pH 2 was used as representative gastric pH value, and since the nature of gastric acid is similar to hydrochloric acid, physiological saline with pH adjusted at 2 by HCl was used to treat the bacteria at 37° C. for 2 hours, then measure population survived and compare with that of the group treated wtih physiological saline at pH 7 to verify their acid tolerance.

(iii) Oxygen tolerance

Changing culturing mode, alter properly activated, inoculate new strains of the present invention into a conventional spiral test tube and culture by standing under non-anaerobic condition for 24 hours, and then, measure OD 600 nm and bacteria population, and compare with those of bacteria cultured under anaerobic condition.

(4) Testing of bacteria survivability:

Homogeneously mixing 1 ml of test sample and 9 ml of dilution solution (aqueous solution of 0.1% peptone and 0.1% agar), preparing a series of appropriate dilutions, adding 1 ml each of dilution solution together with about 20 ml of MRS solid medium (molten state, about 45° C.) into a petri dish, shaking consistantly and standing to solidify; after being completely solidified, placing upside down in an anaerobic jar and culturing at 37° C. for 2–3 days, removing out of the jar and counting.

(5) Culturing method of strains:

The culturing method of strains of the present invention consists of aerobic culturing in skim milk without addition of growth promoting substance, which is favor for industrial production of these strains.

(6) Applications of the strains:

As their applications, strains of the present invention can be used alone or in combination with two or more other lactic acid bacteria (e.g., *Lactobacillus acidophilus, Lactococcus lactis, Lactobacillus casei, Strptococcus thermophilus, Lactobacillus bulgaricus*) or yeast (e.g., *Candida kefyr, Saccharomyces florentinus*) or other usable strains as inoculum in fermentation processes to yield food products such as yogurt, sour milk, frozen yogurt, hactic fermentation beverage or fermented soymilk. The strains of the present invention can be used as food additives to be added during preparation of feedstock, or to be added at latter stage of fermentation process without involved in the fermentation. As such, they can be used in a variety of products such as, milk, concentrated milk, milk powder, ice cream, soymilk, deserts, candy, baby food, products for lactic fermentation milk, and fermentation products described above. The amount added in each kind of product is such as to yield a bacteria count of $10^6$–$10^9$ cfu per gram or milliliter.

In another type of application, strains of the present invention or above-said products containing said strains are used in preparation of frozen or lyophilized powders which contain about $10^9$ or above viable bifidobacteria per gram of product. When yeast powder, carbohydrate or other filler were added into this type of products, tablets or capsules can be prepared therefrom, such as digesting assisted/intenstine conditioning drug or instant food and direct edible bacteria powder.

Effectivenesses of the present invention

The gastric acid-tolerant strains isolated by the invention can pass stomach against gastric acid with increased survivability. And new strains of the present invention are mutant strains of Bifidobacterium, which have resistances against bile salt, gastric acid and oxygen. The oxygen resistance of said strains makes culturing method thereof simplified so that they can be carried out neither anaerobic equipments and operation system, nor continuous nitrogen purging in the course of culturing is necessary, which provides industrial application an improved way with cost saving, process amplification and increased storage survivability. In addition, with combined resistances against gastric acid and bile salt, the requirement of reaching effectively into the intestine after oral administration can be assured such that the function of the product can be promoted.

As the gastrointestinal evnironment (acid, bile salt) resistant and oxygen tolerant mutant strains of Bifidobacterium according to the present invention and fermentation growing method thereof; the related procedure and description other than those described above will be illustrated more substantially in Examples hereinafter, however, the present invention is not limited by these Examples.

EXAMPLE 1

Culturing and Storing of Inoculum

Isolated strains of *Bifidobacterium longum* ATCC 55813 and ATCC 55814 or mutant strains thereof are cultured in MRS (de Man Rogasa and Sharpe) medium. When cultured in liquid state, test tubes having rubber stoppers of anaerobic type are used as vessels (Bellco Glass Inc.) and anaerobic operation system of Virginia Polytechnic Institute (V.P.I.) is used to inoculate strains in an atmosphere of gas mixture of 90% nitrogen and 10% carbon dioxide. When cultured in solid state, the strain is inoculated into a solid culturing medium and then place the medium upside down in an anaerobic jar to culture. Regarding the storing method, strains are inoculated into MRS liquid medium containing 10% glycerol and then frozen stored at −80° C. or are added in 20% skim milk, lyophilized and stored at 4° C. until used.

Composition of MRS medium is as follow:

| | | |
|---|---|---|
| Proteose peptone No. 3 | 10.0 | g |
| Beef extract | 10.0 | g |
| Yeast extract | 5.0 | g |
| Dextrose | 20.0 | g |
| Tween 80 | 1.0 | g |
| Ammonium citrate | 2.0 | g |
| Sodium acetate | 5.0 | g |
| $MgSO_4.7H2O$ | 0.1 | g |
| $MnSO_4.H2O$ | 0.05 | g |
| $K_2HPO_4$ | 2.0 | g |
| Distilled water | 1.0 | L |
| pH to 6.2–6.5 | | |

EXAMPLE 2

Isolation and Screening of Bacterial Strains

Feces of healthy infant were inoculated into two kinds of selective medium of BL-LPIM (BL agar supplemented with lithium chloride 2 g/l, metronidazole 2 mg/l, sodium iodoacetate 0.025 g/l, sodium propionate 3 g/l) and of BIM (Reinforced Clostridial Agar supplemented with nalidixic acid 0.02 g/l, polymyxin B sulfate 0.0085 g/l, kanamycin sulfate 0.05 g/l, sodium iodoacetate 0.025 g/l, 2,3,5-triphenyltetrazolium chloride 0.025 gl), 194 strains of Bifidobacterium spp. were isolated therefrom and then assays of acid, bile salt and oxygen tolerances were carded out, two strains of acid tolerance potential, ATCC 55813 and ATCC 55814, were obtained, both of which were identified by the method recommended in Bergey's Manual as *Bifidobacterium longum*, their bacteriological characteristics are as follow:

1. Morphological characteristics

Gram-positive bacteria, with rod-like bar, Y-shaped, twisted, arc or V-shaped forms under microscopic examination, with occasional expanded form or node. Circular protruded, bright, smooth, white colonies with size of about 1–4 mm are formed on surface of MRS solid medium, while colonies inside the medium appears as circular flying sarcer or star-like triangle; and colonies at the bottom of the medium form white, saw-toothed edged corona shaped metabolic products, with varying size of about 3–8 mm 2. Culturing Characteristics Growth temperature: 25° C.–42° C., optimal temperature: 37°–42° C.

Growth pH 5–9, optimal pH 6.5–7.5

After anaerobic culturing in MRS liquid medium, the ratio of acetic acid/lactic acid formed therein is about 1.5.

3. Physiological properties:

Catalase activity (−), gas generation test (−), milk coagulation activity (+) gelatin hydrolyticity (−), nitrate reducing activity (−), indole formation test (−), hydrogen sulfide generation test (−).

4. Utilization of carbon source

Carbon sources with positive response in fermentation include: xylose, melibiose, galacctose, glucose, arabinose, lactose, fructose, raffinose, maltose, ribose, sucrose, mannose, and melizitose. Those with negative response in fermentation include: mannitol, sorbitol, cellobiose, trehalose, inulin, glycogen, starch, salicin, amygdalin, rhamnose, meso-erythritol, glycerol, meso-inositol and glucuronic acid.

EXAMPLE 3

Improvement of Inoculum (1) UV mutagenesis

After being activated twice in MRS medium at 37° C., inoculate 2%(v/v) each of bacterial suspensions of strains ATCC 55813 and ATCC55814 into 10 ml of broth solution and culture for 18–24 hours, thereafter, harvest bacteria and wash 3 times with 0.1M magnesium sulfate solution, then, resuspende bacteria in the same solution, place bacteria suspension in a sterile glass dish and irradiate the dish under UV Stratalinker™ 1800 (Stratagene) at 250 erg UV dosage. Transfer bacteria suspension in MRS medium and culture overnight, yield mutant strains. Apply 0.2 ml bacteria suspension on screening medium and culture at 37° C. for 3–4 days.

(2) NTG mutagenesis

Culture strains ATCC 55813 and ATCC 55814 in MRS medium and harvest them in a same manner as described above, rinse bacteria twice with 0.1M phosphate buffer solution (pH 7.0), treat with 200 ug/ml of mutation agent, N-methyl-N'-nitro-N-nitrosoguanidine (NTG) at 37° C. for 30 minutes, centrifuge and rinse twice with above-said buffer solution to remove residual NTG, suspend bacteria in MRS medium and culture overnight to yield mutant strains; apply 0.2 ml of thus yielded mutant strains on screening medium and culture at 37° C. for 3–4 days.

(3) Screening medium (i) Acid tolerance screening medium: MRS solid medium having pH adjusted to 4–5 with 4M HCl.

(ii) Bile salt tolerance screening medium: MRS solid medium supplemented with 0.3 %(w/v) oxgall juice.

The thus selected strains having tolerance potential were verified by the above-said tests and were subjected to further mutant screening to produce strains with multiple tolerances, the results were shown in Table III. Mutant strains can gown up to $10^8$–$10^9$ CFU/ml in the presence of bile salt over 24 hours, which was near $10^{6-8}$ fold higher than that of wild type strain. Furthermore, their acid tolerance remained at a level close to that of wild type, such that, after acid treatment, its population decreased only 4 log value, and, additionally, they could grow well under non-anaerobic conditions.

EXAMPLE 4

Scale Up Culturing

Culture mutant strains (e.g., *Bifidobacterium longum* ATCC 55815, ATCC 55816, ATCC 55817, ATCC 55818 )in 10 ml of MRS liquid medium by standing at 37° C. for 18–24 hours, then, inoculate the suspensions at an amount of 1% into 300 ml MRS liquid medium contained in a 500-ml Erlenmeyer flask, culture under same conditions for 18–24 hours, and thereafter, test strains thus yielded with respect to tolerance properties, which showed a tolerance level equal to or even superior than those shown in Table III (small scale culturing).

EXAMPLE 5

Characteristics of New Strains

As described in verification tests, comparison on the difference of bile salt and acid tolerances among new strains according to the present invention and standard strains of same genus, *B. longum* ATCC 15707, *B. bifidum* ATCC 29521, *B. breve* ATCC 15700 and *B. breve* ATCC 15701, results in Table IV shows their higher level of bile salt- and acid-tolerances.

EXAMPLE 6

Culturing of Strains

Sterilizing a 250-ml Erlenmeyer flask containing 125 ml of 12% reduced skim milk at 115° C. for 20 minutes and then inoculating an amount of 2%(v/v) each of new strains according to the present invention and standard strains, culturing them by standing at 37° C. under aerobic condition, sampling periodically and measuring growing bacteria count and pH values. The results were shown in Table V, which indicates that new strains according to the present invention, *B. longum* ATCC 55816, could grow up to $1.14 \times 10^9$ CFU/ml under aerobic condition without additional growth promoting substance 22 hours, and could maintain their growing ability and survivability up to 68 hours with a count of $3.49 \times 10^8$ CFU/mL.

TABLE IV

Comparison of tolerance levels among new strains of the present invention and standard strains

| Strains | Bile salt tolerance Count in log value | | Acid tolerance Count decreased in log value[c] |
|---|---|---|---|
| | Control[a] | Test[b] | |
| *B. bifidum* ATCC 29521 | 8.62 | <3.00 | −5.50 |
| *B. longum* ATCC 15707 | 9.22 | <3.00 | −5.59 |
| *B. breve* ATCC 15700 | 8.88 | 4.04 | −7.33 |
| *B. breve* ATCC 15701 | 8.91 | 4.94 | −8.30 |
| *B. longum* ATCC 55815 | 9.53 | 8.91 | −4.32 |
| *B. longum* ATCC 55816 | 9.26 | 8.85 | −4.06 |
| *B. longum* ATCC 55817 | 9.36 | 8.73 | −3.87 |
| *B. longum* ATCC 55818 | 9.16 | 8.98 | −4.43 |

[a] Viable count of strains cultured in MRS broth for 24 hours.
[b] Viable count of strains sultured in MRS broth + 0.3% oxgall for 24 hours (higher log value indicates better bile salt tolerance).
[c] (count in log value after treating with pH 2.0 physiological saline for 2 hours) − (count in log value after treating with pH 7.0 physiological saline for 2 hours) (less negative value indicates higher acid tolerance).

TABLE III

Tolerance Level of Isolated Strains and Mutant Strains

| Strains | Bile salt tolerance $OD_{600\,nm}$ | | Acid tolerance Count decreased in log value | Oxygen tolerance $OD_{600\,nm}$ | |
|---|---|---|---|---|---|
| | Control[a] | Test b | | Anaerobic | Non anaerobic[d] |
| *B. longum* ATCC 55813 | 2.3668 | 0.1000 | −3.93 | 2.3668 | 2.3560 |
| *B. longum* ATCG 55814 | 2.6511 | 0.1600 | −3.56 | 2.6511 | 1.5020 |
| *B. longum* ATCC 55815 | 2.3634 | 1.5800 | −3.96 | 2.3634 | 2.0490 |
| *B. longum* ATCC 55816 | 2.0054 | 1.4807 | −3.66 | 2.0054 | 1.4834 |
| *B. longum* ATCC 55817 | 2.6920 | 1.6740 | −3.68 | 2.6920 | 2.2320 |
| *B. longum* ATCC 55818 | 2.3832 | 1.2652 | −4.27 | 2.3832 | 1.4629 |

[a] Strains cultured in MRS broth for 24 hours.
[b] Strains cultured in MRS broth +0.3% oxgall for 24 hours.
[c] (count in log value after treating with pH 2.0 physiological saline for 2 hours) − (count in log value after treating with pH 7.0 physiological saline for 2 hours)
[d] Strains cultured in a non-anaerobic spiral tube (MRS broth) for 24 hours (initial $OD_{600\,nm}$ is about 0.2).

TABLE V

Growth of Standard Strains and Mutant Strains Under Aerobic Condition

| Strains | 0 hr | | 22 hr | | 44 hr | | 68 hr | |
|---|---|---|---|---|---|---|---|---|
| | pH | Count CFU/mL | pH | Count CFU/mL | pH | Count CFU/mL | pH | Count CFU/mL |
| *B. bifidum* ATCC 29521 | 6.29 | $8.30 \times 10^6$ | 6.01 | $3.26 \times 10^7$ | 6.02 | $<10^3$ | 6.02 | $<10^3$ |
| *B. longum* ATCC 15707 | 6.13 | $3.30 \times 10^7$ | 5.86 | $<10^5$ | 5.83 | $<10^5$ | 5.82 | $<10^5$ |
| *B. breve* ATCC 15700 | 6.17 | $1.50 \times 10^7$ | 6.02 | $3.11 \times 10^6$ | 5.05 | $3.85 \times 10^7$ | 4.88 | $1.60 \times 10^7$ |
| *B. breve* ATCC 15701 | 6.23 | $1.64 \times 10^7$ | 5.65 | $5.20 \times 10^6$ | 5.52 | $<10^5$ | 5.50 | $<10^5$ |
| *B. longum* ATCC 55813 | 6.14 | $3.00 \times 10^7$ | 6.03 | $<10^4$ | 6.02 | $<10^4$ | 6.01 | — |
| *B. longum* ATCC 55814 | 6.12 | $1.62 \times 10^7$ | 5.95 | $<10^5$ | 5.91 | $<10^5$ | 5.90 | — |

TABLE V-continued

Growth of Standard Strains and Mutant Strains Under Aerobic Condition

| Strains | 0 hr | | 22 hr | | 44 hr | | 68 hr | |
|---|---|---|---|---|---|---|---|---|
| | pH | Count CFU/mL | pH | Count CFU/mL | pH | Count CFU/mL | pH | Count CFU/mL |
| B. longum ATCC 55815 | 6.15 | $5.44 \times 10^7$ | 5.86 | $6.05 \times 10^6$ | 5.72 | $<10^5$ | 5.73 | — |
| B. longum ATCC 55816 | 6.23 | $2.70 \times 10^7$ | 5.16 | $1.14 \times 10^9$ | 3.31 | $2.89 \times 10^9$ | 3.21 | $3.49 \times 10^8$ |
| B. longum ATCC 55817 | 6.16 | $2.22 \times 10^7$ | 5.73 | $2.50 \times 10^6$ | 5.71 | $<10^5$ | 5.70 | — |
| B. longum ATCC 55818 | 6.14 | $2.86 \times 10^7$ | 5.98 | $3.58 \times 10^6$ | 5.96 | $<10^4$ | 5.96 | — |

What is claimed is:

1. An isolated strain of bacteria, which is *Bifidobacterium longum* Y1 (ATCC 55813).

2. An isolated strain of bacteria, which is *Bifidobacterium longum* Y2 (ATCC 55814).

3. An isolated strain of bacteria, which is *Bifidobacterium longum* Y1-2E-05 (ATCC 55815).

4. An isolated strain of bacteria, which is *Bifidobacterium longum* Y1-4A-01 (ATCC 55816).

5. An isolated strain of bacteria, which is *Bifidobacterium longum* Y1-1A-01 (ATCC 55817).

6. An isolated strain of bacteria, which is *Bifidobacterium longum* Y1-2B-04 (ATCC 55818).

7. A method of culturing a strain of *Bifidobacterium longum*, comprising aerobically culturing a strain according to any one of claims 1–6 in skim milk at a temperature of 25°–45° C.

8. A food composition comprising the strain according to any one of claims 1–6, added directly to foodstock.

9. The food composition of claim 8, wherein said foodstock is selected from the group consisting of concentrated milk, milk powder, ice cream, cream butter, cheese, vegetable juice, fruit juice, dessert, candy, baby food, yogurt, sour milk, frozen yogurt and fermented soymilk.

10. A fermentation method for producing a food product, comprising inoculating a strain according to any one of claims 1–6 to a fermentation medium to produce said food product.

11. The method of claim 10 wherein said food product is selected from the group consisting of yogurt, sour milk, frozen yogurt, and fermented soymilk.

12. The food composition of claim 8 wherein said foodstock is milk or soymilk.

* * * * *